United States Patent
Lippa et al.

(10) Patent No.: US 7,098,229 B2
(45) Date of Patent: *Aug. 29, 2006

(54) (+)-1-(3,4-DICHLOROPHENYL)-3-AZABICYCLO[3.1.0]HEXANE, COMPOSITIONS AND USES THEREOF

(75) Inventors: Arnold S. Lippa, Ridgewood, NJ (US); Joseph W. Epstein, Monroe, NY (US)

(73) Assignee: DOV Pharmaceutical, Inc., Hackensack, NJ (US)

( * ) Notice: Subject to any disclaimer, the term of this patent is extended or adjusted under 35 U.S.C. 154(b) by 204 days.

This patent is subject to a terminal disclaimer.

(21) Appl. No.: 10/466,457

(22) PCT Filed: Jan. 11, 2002

(86) PCT No.: PCT/US02/00845

§ 371 (c)(1), (2), (4) Date: Feb. 10, 2004

(87) PCT Pub. No.: WO02/066427

PCT Pub. Date: Aug. 29, 2002

(65) Prior Publication Data

US 2004/0132797 A1    Jul. 8, 2004

(51) Int. Cl.
*A61K 31/403* (2006.01)
*C07D 209/52* (2006.01)

(52) U.S. Cl. ...................... 514/412; 548/452
(58) Field of Classification Search ........... 514/412; 548/452
See application file for complete search history.

(56) References Cited

U.S. PATENT DOCUMENTS

| | | | |
|---|---|---|---|
| 3,892,772 A | 7/1975 | Hofmann et al. | 260/326.5 |
| 4,022,652 A | 5/1977 | Hirano et al. | 117/22 |
| 4,088,652 A | 5/1978 | Fanshawe et al. | 548/515 |
| 4,118,393 A | 10/1978 | Fanshawe et al. | 548/512 |
| 4,118,417 A | 10/1978 | Epstein | 562/401 |
| 4,131,611 A | 12/1978 | Fanshawe et al. | 548/515 |
| 4,196,120 A | 4/1980 | Fanshawe et al. | 558/46 |
| 4,231,935 A | 11/1980 | Fanshawe et al. | 548/515 |
| 4,435,419 A | 3/1984 | Epstein et al. | 514/412 |
| 5,130,430 A | 7/1992 | Shaw | 544/346 |
| 6,194,000 B1 | 2/2001 | Smith et al. | 424/458 |
| 6,204,284 B1 | 3/2001 | Beer et al. | 514/412 |

*Primary Examiner*—Kamal A. Saeed
*Assistant Examiner*—Jason M. Nolan
(74) *Attorney, Agent, or Firm*—Jeffrey J. King; Black Lowe & Graham PLLC

(57) ABSTRACT

The present invention relates to (+)-1-(3,4-dichlorophenyl)-3-azabicyclo[3.1.0]hexane and pharmaceutically acceptable salts thereof, compositions comprising (+)-1-(3,4-dichlorophenyl)-3-azabicyclo[3.1.0]hexane or a pharmaceutically acceptable salt thereof, and methods for treating of or preventing relapse of depression, anxiety disorders, eating disorders, or urinary incontinence in a patient comprising administering (+)-1-(3,4-dichlorophenyl)-3-azabicyclo[3.1.0]hexane or a pharmaceutically acceptable salt thereof. The (+)-1-(3,4-dichlorophenyl)-3-azabicyclo[3.1.0]hexane or pharmaceutically acceptable salt thereof is preferably substantially free of its corresponding (−)-enantiomer.

18 Claims, No Drawings

US 7,098,229 B2

(+)-1-(3,4-DICHLOROPHENYL)-3-AZABICYCLO[3.1.0]HEXANE, COMPOSITIONS AND USES THEREOF

This application is the U.S. National Phase of PCT/US02/00845, filed Jan. 11, 2002 and claims benefit to U.S. application Ser. No. 09/758,883, filed on Jan. 11, 2001, now U.S. Pat. No. 6,372,919, issued on Apr. 16, 2002, of which all are incorporated herein by reference in their entirety.

1. FIELD OF THE INVENTION

The present invention relates to (+)-1-(3,4-dichlorophenyl)-3-azabicyclo[3.1.0]hexane and pharmaceutical salts thereof, compositions comprising (+)-1-(3,4-dichlorophenyl)-3-azabicyclo[3.1.0]hexane or a pharmaceutically acceptable salt thereof and methods for treating of or preventing relapse of depression, anxiety disorders, eating disorders, or urinary incontinence in a patient comprising administering to a patient (+)-1-(3,4-dichlorophenyl)-3-azabicyclo[3.1.0]hexane or a pharmaceutically acceptable salt thereof.

2. BACKGROUND OF THE INVENTION

Depression is one of the most common of the mental illnesses, having morbidity rate of over 10% in the general population. Depression is characterized by feelings of intense sadness, despair, mental slowing, loss of concentration, pessimistic worry, agitation, and self-deprecation (*Harrison's Principles of Internal Medicine* 2490–2497 (Fauci et al. eds., 14th ed. 1998)). Depression can have physical manifestations including insomnia, hypersomnia, anorexia, weight loss, overeating, decreased energy, decreased libido, and disruption of normal circadian rhythms of activity, body temperature, and endosine functions. In fact, as many as 10% to 15% of depressed individuals display suicidal behavior. R. J. Baldessarini, *Drugs and the Treatment of Psychiatric Disorders: Depression and Mania*, in Goodman and Gilman's *The Pharmacological Basis of Therapeutics* 431 (9$^{th}$ ed. 1996).

U.S. Pat. No. 4,435,419 to Epstein et al. discloses racemic, (±)-1-(3,4-dichlorophenyl)-3-azabicyclo[3.1.0]hexane for use as an anti-depressant agent.

Administration of a racemic, i.e., 50:50, mixture of the (+)- and the (−)-enantiomer of any drug, for example (±)-1-(3,4-dichlorophenyl)-3-azabicyclo[3.1.0]hexane, to a patient can be disadvantageous. First, the racemic mixture might be less pharmacologically active than one of its enantiomers, rendering racemic drugs inherently inefficient. Second, the racemic mixture may be more toxic to a patient than one of its enantiomers, so that administration of a racemic mixture can lead to undesirable side effects in a patient.

Accordingly, there is a clear need in the art for an enantiomer of (±)-1-(3,4-dichlorophenyl)-3-azabicyclo[3.1.0]hexane, the enantiomer being preferably substantially free of the corresponding opposite enantiomer, which would overcome one or both of the aforementioned disadvantages.

Citation of identification of any reference in Section 2 of this application is not to be construed as an admission that such reference is prior art to the present application.

3. SUMMARY OF THE INVENTION

In one embodiment, the invention provides (+)-1-(3,4-dichlorophenyl)-3-azabicyclo[3.1.0]hexane and pharmaceutically acceptable salts thereof. (+)-1-(3,4-dichlorophenyl)-3-azabicyclo[3.1.0]hexane and pharmaceutically acceptable salts thereof are useful for treating of or preventing relapse of depression in a patient.

The present invention further provides compositions comprising an effective amount of (+)-1-(3,4-dichlorophenyl)-3-azabicyclo[3.1.0]hexane or a pharmaceutically acceptable salt thereof. The present compositions can additionally comprise a pharmaceutically acceptable vehicle. These compositions are useful for treating of or preventing relapse of depression in a patient.

In another embodiment, the invention provides a method for treating of or preventing relapse of depression in a patient, comprising administering to a patient in need of such treatment or prevention an effective amount of (+)-1-(3,4-dichlorophenyl)-3-azabicyclo[3.1.0]hexane or a pharmaceutically acceptable salt thereof.

In still another embodiment, the invention provides a method for treating of or preventing relapse of anxiety disorders, eating disorders, or urinary incontinence in a patient, comprising administering to a patient in need of such treatment or prevention an effective amount of (+)-1-(3,4-dichlorophenyl)-3-azabicyclo[3.1.0]hexane or a pharmaceutically acceptable salt thereof.

Preferably, (+)-1-(3,4-dichlorophenyl)-3-azabicyclo[3.1.0]hexane or a pharmaceutically acceptable salt thereof, particularly when used in the present methods or compositions, is substantially free of its corresponding (−)-enantiomer, (−)-1-(3,4-dichlorophenyl)-3-azabicyclo[3.1 0]hexane. This enantiopurity can be achieved through the use of chromatographic resolution techniques such as chiral chromatography or simulated moving bed technology, or via chemical separation through the employment of optically active resolving agents.

The present invention may be understood more fully by reference to the detailed description and examples, which are intended to exemplify non-limiting embodiments of the invention.

4. DETAILED DESCRIPTION OF THE INVENTION

Applicants have discovered that (+)-1-(3,4-dichlorophenyl)-3-azabicyclo[3.1.0]hexane and pharmaceutically acceptable salts thereof are surprisingly and unexpectedly more active than (±)-1-(3,4-dichlorophenyl)-3-azabicyclo[3.1.0]hexane for treating of or preventing relapse of depression in a patient.

4.1. DEFINITIONS

The term "substantially free of its corresponding (−)-enantiomer" means containing no more than about 5% w/w of the corresponding (−)-enantiomer, preferably no more than about 2% w/w of the corresponding (−)-enantiomer, more preferably no more than about 1% w/w of the corresponding (−)-enantiomer.

The term "corresponding (−)-enantiomer" when used in connection with (+)-1-(3,4-dichlorophenyl)-3-azabicyclo[3.1.0]hexane or a pharmaceutically acceptable salt thereof means "(−)-1-(3,4-dichlorophenyl)-3-azabicyclo[3.1.0]hexane" or a pharmaceutically acceptable salt thereof.

A "patient" is an animal, including, but not limited to, an animal such a cow; monkey, horse, sheep, pig, chicken, turkey, quail, cat, dog, mouse, rat, rabbit, and guinea pig, and is more preferably a mammal, and most preferably a human.

The phrase "pharmaceutically acceptable salt," as used herein is a salt formed from an acid and the basic nitrogen group of (+)-1-(3,4-dichlorophenyl)-3-azabicyclo[3.1.0] hexane. Preferred salts include, but not limited, to sulfate, citrate, acetate, oxalate, chloride, bromide, iodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

4.2 (+)-1-(3,4-DICHLOROPHENYL)-3-AZABICYCLO[3.1.0]HEXANE (+)-1-(3,4-Dichlorophenyl)-3-azabicyclo[3.1.0]hexane, preferably that substantially free of its corresponding (−)-enantiomer, can be obtained from (±)-1-(3,4-dichlorophenyl)-3-azabicyclo[3.1.0]hexane using chiral chromatographic methods, such as high-performance liquid chromatography ("HPLC") with a suitable, preferably chiral, column (±)-1-(3,4-Dichlorophenyl)-3-azabicyclo[3.1.0]hexane is obtainable using methods disclosed in U.S. Pat. No. 4,435,419 to Epstein et al.

In a preferred embodiment, (+)-1-(3,4-dichlorophenyl)-3-azabicyclo[3.1.0]hexane is obtained by resolving (±)-1-(3, 4-dichlorophenyl)-3-azabicyclo[3.1.0]hexane using a chiral polysaccharide stationary phase and an organic eluent. Preferably, the polysaccharide is starch or a starch derivative. Advantageously, a chiral HPLC column can be used, for example, a CHIRALPAK AD column manufactured by Daicel and commercially available from Chiral Technologies, Inc., Exton, Pa., more preferably a 1 cm×25 cm CHIRALPAK AD HPLC column. The preferred eluent is a hydrocarbon solvent adjusted in polarity with a miscible polar organic solvent. Preferably, the organic eluent contains a non-polar, hydrocarbon solvent present in about 95% to about 99.5% (volume/volume) and a polar organic solvent present in about 5 to about 0.5% (volume/volume). In a preferred embodiment, the hydrocarbon solvent is hexane and the miscible polar organic solvent is isopropylamine.

In another preferred embodiment, an alternative chromatographic procedure, known as simulated moving bed (SMB) chromatography can be employed for the resolution (±)-1-(3,4-dichlorophenyl)-3-azabicyclo[3.1.0]hexane. SMB is increasingly becoming the method of choice for large-scale enantiomer separation in the pharmaceutical industry (See Chemical and Engineering News, 2001, Vol. 79, No. 20, p 47).

In yet another preferred embodiment, the resolution of racemic (±)-1-(3,4-dichlorophenyl)-3-azabicyclo[3.1.0]hexane to obtain (+)-1-(3,4-dichlorophenyl)-3-azabicyclo[3.1.0]hexane may be achieved via the use of optically active resolving acids via the formation of and subsequent separation of the resulting diasteromeric salts. Commonly employed chiral acids for this purpose include: tartaric and O-acyl tartaric acids, mandelic acid and O-substituted mandelic acids, 1,1'-binaphthyl-2,2'-diyl hydrogen phosphate, camphoric acid, camphor sulfonic acid, and other readily-available optically active acids (both commercially available and readily synthesized).

For a general discussion of the separation of stereoisomers, see Eliel and Wilen, STEREOCHEMISTRY OF ORGANIC COMPOUNDS; Wiley: New York 1994, p 297–464, and references cited herein.

4.3. THERAPEUTIC USES OF (+)-1-(3,4-DICHLOROPHENYL)-3-AZABICYCLO[3.1.0]HEXANE

In accordance with the invention, (+)-1-(3,4-dichlorophenyl)-3-azabicyclo[3.1.0]hexane or a pharmaceutically acceptable salt thereof is administered to a patient, preferably a mammal, more preferably a human, for the treatment or prevention of disorders, including but not limited to, depression, anxiety disorders, eating disorders and urinary incontinence disorders. In one embodiment, "treatment" or "treating" refers to an amelioration of such a disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of such a disorder, either physically, e.g., normalization of a discernible symptom, physiologically, e.g., normalization of a physical parameter, or both. In yet another embodiment, "treatment" or "treating" refers to delaying the onset of such a disorder.

4.3.1 ALLEVIATION OF DEPRESSION USING (+)-1-(3,4-DICHLOROPHENYL)-3-AZABICYCLO[3.1.0]HEXANE

In certain embodiments, (+)-1-(3,4-dichlorophenyl)-3-azabicyclo[3.1.0]-hexane or a pharmaceutically acceptable salt thereof is administered to a patient, preferably a mammal, more preferably a human, as a preventative measure against relapse of depression. As used herein, "prevention" or "preventing" refers to a reduction of the risk of occurrence of relapse in a patient suffering from depression. In one embodiment, (+)-1-(3,4-dichlorophenyl)-3-azabicyclo[3.1.0]hexane or a pharmaceutically acceptable salt thereof is administered to a patient as a preventative measure against relapse. According to this embodiment, the patient can have a genetic predisposition to depression, such as a family history of biochemical imbalance in the brain, or a non-genetic predisposition to depression. Accordingly, the (+)-1-(3,4-dichlorophenyl)-3-azabicyclo[3.1.0]hexane and pharmaceutically acceptable salts thereof can be used for the treatment of one manifestation of depression and prevention of another.

(+)-1-(3,4-Dichlorophenyl)-3-azabicyclo[3.1.0]hexane and pharmaceutically acceptable salts thereof are also useful for treating of or preventing relapse of endogenous depression, unipolar depression, retarded depression, agitated depression, bipolar depression, post-partum depression, depression with anxiety, depression with obsessiveness, depression with an illness causing seizures, dysthymia, seasonal affective disorder, diurnal mood variations, depression associated with menopause, and depression in association with medical illness, alcohol, or substance abuse.

4.3.2 ALLEVIATION OF ANXIETY DISORDERS USING (+)-1-(3,4-DICHLOROPHENYL)-3-AZABICYCLO[3.1.0]HEXANE (+)-1-(3,4-dichlorophenyl)-3-azabicyclo[3.1.0]hexane and pharmaceutically acceptable salts thereof are also useful for treating of or preventing relapse of anxiety disorders (for an overview on anxiety disorders, see Derogatis L. R. & Wise, T. N., "Anxiety and Depressive Disorders in the Medical Patient," Washington, D.C., American Psychiatric Press, 1989, and references cited herein). Such disorders include, but are not limited to, Panic Disorder; Panic Attack; Agoraphobia; Generalized Anxiety Disorder; Obsessive-Compulsive Disorders; Phobic Disorders and Post-Traumatic Stress Disorders, some of which are further subclassified as listed below.

Phobic-related Disorders include, but are not limited to, specific phobias, such as Acrophobia, Algophobia, Arachnophobia, Astraphobia, Aviaphobia, Claustrophobia, Cynophobia, Demophobia, Hematophobia, Monophobia, Nyctophobia, Pathophobia, Pyrophobia, Thanatophobia and Zoophobia; General Social Phobia; Specific Social Phobia and Phobic Disorder not otherwise specified (NOS).

Obsessive-Compulsive-related Disorders include, but are not limited to, Trichotillomania, Body Dysmorphic Disorder, Habit Disorders, Tic Disorders; Tourette's Syndrome and Obsessive-Compulsive Disorder not otherwise specified (NOS).

Post-traumatic-related Disorders include, but are not limited to, Acute Stress Disorder; and Post-Traumatic Disorder not otherwise specified (NOS).

4.3.3 OTHER DISORDERS ALLEVIATED USING (+)-1-(3,4-DICHLOROPHENYL)-3-AZABICYCLO[3.1.0]HEXANE

Disorders alleviated through the use of (+)-1-(3,4-dichlorophenyl)-3-azabicyclo[3.1.0]hexane also include eating disorders and urinary incontinence and are not limited to the specific disorders described herein, as many types of disorders may manifest from a particular primary disorder. For example, as disclosed in U.S. Pat. No. 6,132,724 to Blum, attention deficit hyperactivity disorder may manifest itself in the form of alcohol abuse, drug abuse, obsessive compulsive behaviors, learning disorders, reading problems, gambling, manic symptoms, phobias, panic attacks, oppositional defiant behavior, conduct disorder, academic problems in school, smoking, abnormal sexual behaviors, schizoid behaviors, somatization, depression, sleep disorders, general anxiety, stuttering, and tics disorders. Additionally, clinical terms used herein for many specific disorders are found in the Quick Reference to the Diagnostic Criteria From DSM-IV (Diagnostic and Statistical Manual of Mental Disorders, Fourth Edition), The American Psychiatric Association, Washington, D.C., 1994, 358 pages. Specific disorders related to the indicated disorders can be found in this reference. In addition, a detailed discussion of eating disorders can be found in . . . For further discussion on urinary incontinence and related conditions, see Eating disorders include, but are not limited to, Anorexia Nervosa; Binge-Eating Disorder; Bulimia Nervosa, Non-purging Type; Bulimia Nervosa, Purging Type; and Eating Disorder not otherwise specified (NOS).

Urinary incontinence includes, but is not limited to, Urge Incontinence; Stress Incontinence; Overflow Incontinence; Functional Incontinence; Neurogenic Incontinence and Post-Prostatectomy Incontinence.

4.4. THERAPEUTIC/PROGHYLACTIC ADMINISTRATION AND COMPOSITION OF THE INVENTION

Due to their activity, (+)-1-(3,4-dichlorophenyl)-3-azabicyclo[3.1.0]hexane and pharmaceutically acceptable salts thereof are advantageously useful in veterinary and human medicine. As described above, (+)-1-(3,4-dichlorophenyl)-3-azabicyclo[3.1.0]hexane and pharmaceutically acceptable salts thereof are useful for the treatment of or prevention of relapse of depression, anxiety disorders, eating disorders and urinary incontinence-related disorders in a patient.

When administered to a patient, (+)-1-(3,4-dichlorophenyl)-3-azabicyclo[3.1.0]hexane or a pharmaceutically acceptable salt thereof is preferably administered as component of a composition that optionally comprises a pharmaceutically acceptable vehicle. The present compositions, which comprise (+)-1-(3,4-dichlorophenyl)-3-azabicyclo [3.1.0]hexane or a pharmaceutically acceptable salt thereof, are preferably administered orally. The compositions of the invention may also be administered by any other convenient route, for example, by infusion or bolus injection, by absorption through epithelial or mucocutaneous linings (e.g., oral mucosa, rectal, and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer (+)-1-(3,4-dichlorophenyl)-3-azabicyclo[3.1.0] hexane and pharmaceutically acceptable salts thereof.

In certain embodiments, the present compositions can comprise (+)-1-(3,4-dichlorophenyl)-3-azabicyclo[3.1.0] hexane and/or one or more pharmaceutically acceptable salts thereof.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of (+)-1-(3,4-dichlorophenyl)-3-azabicyclo[3.1.0]hexane or a pharmaceutically acceptable salt thereof into the bloodstream.

In specific embodiments, it may be desirable to administer (+)-1-(3,4-dichlorophenyl)-3-azabicyclo[3.1.0]hexane or a pharmaceutically acceptable salt thereof locally. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce (+)-1-(3,4-dichlorophenyl)-3-azabicyclo[3.1.0]hexane or a pharmaceutically acceptable salt thereof into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, (+)-1-(3,4-dichlorophenyl)-3-azabicyclo[3.1.0]hexane and pharmaceutically acceptable salts thereof can be formulated as a suppository, with traditional binders and vehicles such as triglycerides.

In another embodiment, (+)-1-(3,4-dichlorophenyl)-3-azabicyclo[3.1.0]hexane and pharmaceutically acceptable salts thereof can be delivered in a vesicle, in particular a liposome (see Langer, 1990, *Science* 249:1527–1533; Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.).

In yet another embodiment, (+)-1-(3,4-dichlorophenyl)-3-azabicyclo[3.1.0]hexane and pharmaceutically acceptable salts thereof can be delivered in a controlled release system (see, e.g., Goodson, in Medical Applications of Controlled Release, supra, vol. 2, pp. 115–138 (1984)). Other controlled-release systems discussed in the review by Langer, 1990, *Science* 249:1527–1533) may be used. In one embodiment, a pump may be used (see Langer, supra; Sefton, 1987, *CRC Crit. Ref. Biomed. Eng.* 14:201; Buchwald et al., 1980, *Surgery* 88:507 Saudek et al., 1989, *N. Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled-release system can be placed in proximity of a target of (+)-1-(3,4-dichlorophenyl)-3-azabicyclo[3.1.0] hexane or a pharmaceutically acceptable salt thereof, e.g., the spinal column or brain, thus requiring only a fraction of the systemic dose.

The present compositions can optionally comprise a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, mammals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in *Remington's Pharmaceutical Sciences,* Alfonso R. Gennaro ed., Mack Publishing Co. Easton, Pa., 19th ed., 1995, pp. 1447 to 1676, incorporated herein by reference.

In a preferred embodiment, (+)-1-(3,4-dichlorophenyl)-3-azabicyclo[3.1.0]hexane or a pharmaceutically acceptable salt thereof is formulated in accordance with routine procedures as a pharmaceutical composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharin, cellulose and magnesium carbonate. Such vehicles are preferably of pharmaceutical grade. Typically, compositions for intravenous administration comprise sterile isotonic aqueous buffer. Where necessary, the compositions may also include a solubilizing agent.

In another embodiment, (+)-1-(3,4-dichlorophenyl)-3-azabicyclo[3.1.0]hexane or a pharmaceutically acceptable salt thereof can be formulated for intravenous administration. Compositions for intravenous administration may optionally include a local anesthetic such as lignocaine to lessen pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where (+)-1-(3,4-dichlorophenyl)-3-azabicyclo[3.1.0]hexane or a pharmaceutically acceptable salt thereof is to be administered by infusion, it can be dispensed, for example, with an infusion bottle containing sterile pharmaceutical grade water or saline. Where the (+)-1-(3,4-dichlorophenyl)-3-azabicyclo[3.1.0]hexane or a pharmaceutically acceptable salt thereof is administered by injection, an ampoule of sterile water for injection or saline can be provided so that the ingredients may be mixed prior to administration.

The amount of (+)-1-(3,4-dichlorophenyl)-3-azabicyclo[3.1.0]hexane or a pharmaceutically acceptable salt thereof that will be effective in the treatment of a particular depression disorder, anxiety disorder, eating disorder or urinary incontinence related disorder, will depend on the nature of the disorder or condition, and can be determined by standard clinical techniques. In addition, in vitro or in vivo assays may optionally be employed to help identify optimal dosage ranges. The precise dose to be employed will also depend on the route of administration, and the seriousness of the disease or disorder, and should be decided according to the judgment of the practitioner and each patient's circumstances. However, suitable dosage ranges for oral administration are generally about 0.2 milligram to about 2.0 milligrams of (+)-1-(3,4-dichlorophenyl)-3-azabicyclo[3.10]hexane or a pharmaceutically acceptable salt thereof per kilogram body weight per day. In specific preferred embodiments of the invention, the oral dose is about 0.01 milligram to about 100 milligrams per kilogram body weight per day, more preferably about 0.1 milligram to about 75 milligrams per kilogram body weight per day, more preferably about 0.5 milligram to about 50 milligrams per kilogram body weight per day, and yet more preferably about 1 milligram to about 30 milligrams per kilogram body weight per day. In another preferred embodiment, the oral dose is about 1 milligram to about 3 milligrams of (+)-1-(3,4-dichlorophenyl)-3-azabicyclo[3.1.0]hexane or a pharmaceutically acceptable salt thereof of the invention per kilogram body weight per day. The dosage amounts described herein refer to total amounts administered; that is, if (+)-1-(3,4-dichlorophenyl)-3-azabicyclo[3.1.0]hexane and/or one or more pharmaceutically acceptable salts thereof are administered, the preferred dosages correspond to the total amount administered. Oral compositions preferably contain about 10% to about 95% active ingredient by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. Suitable dosage ranges for intranasal administration are generally about 0.01 pg/kg body weight per day to about 1 mg/kg body weight per day. Suppositories generally contain about 0.01 milligram to about 50 milligrams of (+)-1-(3,4-dichlorophenyl)-3-azabicyclo[3.1.0]hexane or a pharmaceutically acceptable salt thereof per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 200 milligrams per kilogram of body weight per day. Suitable doses for topical administration are in the range of about 0.001 milligram to about 1 milligram, depending on the area of administration. Effective doses may be extrapolated from dose-response curves derived from in vitro or animal model test systems. Such animal models and systems are well known in the art.

The invention also provides pharmaceutical packs or kits comprising one or more vessels containing (+)-1-(3,4-dichlorophenyl)-3-azabicyclo[3.1.0]hexane or a pharmaceutically acceptable salt thereof. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains (+)-1-(3,4-dichlorophenyl)-3-azabicyclo[3.1.0]hexane and/or one or more pharmaceutically acceptable salts thereof. In another embodiment, the kit comprises a therapeutic agent and (+)-1-(3,4-dichlorophenyl)-3-azabicyclo[3.1.0]hexane or a pharmaceutically acceptable salt thereof.

(+)-1-(3,4-Dichlorophenyl)-3-azabicyclo[3.1.0]hexane and pharmaceutically acceptable salts thereof are preferably assayed in vitro or in vivo, for the desired therapeutic or prophylactic activity, prior to use in humans. For example, in vitro assays can be used to determine whether it is preferable to administer (+)-1-(3,4-dichlorophenyl)-3-azabicyclo[3.1.0]hexane, a pharmaceutically acceptable salt thereof, and/or another therapeutic agent. Animal model systems can be used to demonstrate safety and efficacy.

Other methods will be known to the skilled artisan and are within the scope of the invention.

4.5. COMBINATION THERAPY

In certain embodiments of the present invention, (+)-1-(3,4-dichlorophenyl)-3-azabicyclo[3.1.0]hexane or a pharmaceutically acceptable salt thereof can be used in combination therapy with at least one other therapeutic agent. (+)-1-(3,4-Dichlorophenyl)-3-azabicyclo[3.1.0]hexane or a pharmaceutically acceptable salt thereof and the other therapeutic agent can act additively or, more preferably, synergistically. In a preferred embodiment, a composition comprising (+)-1-(3,4-dichlorophenyl)-3-azabicyclo[3.1.0]hexane or a pharmaceutically acceptable salt thereof is administered concurrently with the administration of another therapeutic agent, which can be part of the same composition as or in a different composition from that comprising (+)-1-(3,4-dichlorophenyl)-3-azabicyclo[3.1.0]hexane or a pharmaceutically acceptable salt thereof. In another embodiment, a composition comprising (+)-1-(3,4-dichlorophenyl)-3-azabicyclo[3.1.0]hexane or a pharmaceutically acceptable salt thereof is administered prior or subsequent to administration of another therapeutic agent. As many of the disorders for which (+)-1-(3,4-dichlorophenyl)-3-azabicyclo[3.1.0]hexane and pharmaceutically acceptable salts thereof are useful in treating are chronic, in one embodiment combination therapy involves alternating between administering a composition comprising a (+)-1-(3,4-dichlorophenyl)-3-azabicyclo[3.1.0]hexane or a pharmaceutically acceptable salt thereof and a composition comprising another therapeutic agent. The duration of administration of (+)-1-(3,4-dichlorophenyl)-3-azabicyclo[3.1.0]hexane, a pharmaceutically acceptable salt thereof, or the other therapeutic agent can be, e.g., one month, three months, six months, a year, or for more extended periods, such as the patient's lifetime. In certain embodiments, when a composition of the invention is administered concurrently with another therapeutic agent that potentially produces adverse side effects including, but not limited to, toxicity, the other therapeutic agent can advantageously be administered at a dose that falls below the threshold at which the adverse side effect is elicited.

The other therapeutic agent can be an anti-depressant agent. Useful anti-depressant agents include, but are not limited to, amitriptyline, clomipramine, doxepine, imipramine, trimipramine, amoxapine, desipramine, maprotiline, nortriptyline, protripyline, fluoxetine, fluvoxamine, paroxetine, setraline, venlafaxine, bupropion, nefazodone, trazodone, pheuelzine, tranylcypromine and selegiline.

The other therapeutic agent can be an anxiolytic agent. Useful anxiolytic agents include, but are not limited to, benzodiazepines, such as alprazolam, chlordiazepoxide, clonazepam, clorazepate, diazepam, halazepam, lorazepam, oxazepam, and prazepam; non-benzodiazepine agents, such as buspirone; and tranquilizers, such as barbituates.

The other therapeutic agent can be an antipsychotic drug. Useful antipsychotic drugs include, but are not limited to, phenothiazines, such as chlorpromazine, mesoridazine besylate, thioridazine, acetophenazine maleate, fluphenazine, perphenazine, and trifluoperazine; thioxanthenes, such as chlorprothixene, and thiothixene; and other hetercyclic compounds, such as clozapine, haloperidol, loxapine, molindone, pimozide, and risperidone. Preferable anti-psychotic drugs include chlorpromazine HCl, thioridazine HCl, fluphenazine HCl, thiothixene HCl, and molindone HCl.

The other therapeutic agent can be an anti-obesity drug. Anti-obesity drugs for use in combination with the compounds of the invention include, but are not limited, to β-adrenergic receptor agonists, preferably β-3 receptor agonists: fenfluramine; dexfenfluramine; sibutramine; bupropion; fluoxetine; phentermine; amphetamine; methamphetamine; dextroamphetamine; benzphetamine; phendimetrazine; phenmetrazine; diethylpropion; mazindol; and phenylpropanolamine.

5. EXAMPLE

(+)-1-(3,4-DICHLOROPHENYL)-3-AZABICYCLO[3.1.0]HEXANE

5.1 RESOLUTION OF THE RACEMATE VIA CHIRAL CHROMATOGRAPHY

To 279 mg of (±)-1-(3,4-dichlorophenyl)-3-azabicyclo[3.1.0]hexane hydrochloride obtained using the methods described in Epstein et al., *J. Med. Chem.*, 24:481–490 (1981) was added 7 mL of 9:1 hexane:isopropyl alcohol, followed by 8 drops of diethylamine. To the resulting mixture was added isopropyl alcohol, dropwise, until a solution was obtained. The solution was concentrated to a volume of 6 mL using a stream of helium gas, and six 1-mL portions of the concentrate were subjected to high-performance liquid chromatography using an HPLC instrument equipped with a 1 cm×25 cm Daicel CHIRALPAK AD column (Chiral Technologies, Inc., Exton, Pa.). Elution was carried out at ambient temperature using 95:5 (v/v) hexane:isopropyl alcohol solution containing 0.05% diethylamine as a mobile phase at a flow rate of 6 mL/min. The fraction eluting at about 21.5 to 26 minutes was collected and concentrated to provide a first residue, which was dissolved in a minimal amount of ethyl acetate. Using a stream of nitrogen, the ethyl acetate solution was evaporated to provide a second residue, which was dissolved in 1 mL of diethyl ether. To the diethyl ether solution was added 1 mL diethyl ether saturated with gaseous hydrochloric acid. A colorless precipitate formed, which was filtered, washed with 2 mL of diethyl ether and dried to provide 73.4 mg of (+)-1-(3,4-dichlorophenyl)-3-azabicyclo[3.1.0]hexane hydrochloride: optical rotation $[\alpha]^{25}_D$=+60° in methanol at 2 mg/mL; 99.7% enantiomeric excess.

5.2 RESOLUTION OF THE RACEMATE VIA THE USE OF L-DI-(O-BENZOYL) TARTARIC ACID AS A CHIRAL RESOLVING AGENT

A 2.68 g (0.0101 mol) sample of (±)-1-(3,4-dichlorophenyl)-3-azabicyclo[3.1.0]hexane hydrochloride as described in Epstein, et al., J. Med. Chem., 1981, 24, pp. 481–490, was dissolved in 50 mL of water and this solution was made basic to pH 11 with 10N sodium hydroxide solution, and the precipitated free base was extracted into 25 mL of dichloromethane. This solution was dried over sodium sulfate and filtered. To this filtrate, was added a solution of 3.70 g (0.1030 mol) of L-di-(O-benzoyl)tartaric acid in 25 mL of methanol, and this solution was boiled until crystallization ensued. The mixture was cooled to room temperature and allowed to stand for one hour. The crystals were collected to give 3.21 g of colorless crystals which were boiled in 50 mL of methanol, and this mixture was cooled in an ice bath, then filtered to give 2.04 g of colorless crystals, m.p. 185–187° C. of (+)-1-(3,4-dichlorophenyl)-3-azabicyclo[3.1.0]hexane monosalt with L-di-(O-benzoyl) tartaric acid. This salt was stirred with 5N aqueous sodium hydroxide and the liberated free base was extracted into ethyl acetate. The organic layer was washed with dilute aqueous sodium hydroxide solution, then water, and then dried over sodium sulfate. This was filtered, and the filtrate was treated with a solution of HCl in ether until precipitation ceased. The crystals were collected by filtration and air dried to yield 0.748 g of (+)-1-(3,4-dichlorophenyl)-3-azabicyclo[3.1.0]hexane hydrochloride as colorless crystals, m.p. 173–173° C., (α)=+64.2°, C=6.7, MeOH, which was substantially free of the corresponding (−)-enantiomer.

6. EXAMPLE

ACTIVITY COMPARISON OF (+)-1-(3,4-DICHLOROPHENYL)-3-AZABICYCLO[3.1.0] HEXANE AND (±)-1-(3,4-DICHLOROPHENYL)-3-AZABICYCLO[3.1.0]HEXANE

6.1. NOREPINEPHRINE TRANSPORTER BINDING ASSAY

The anti-depressant properties of (+)-1-(3,4-dichlorophenyl)-3-azabicyclo[3.1.0]hexane hydrochloride were compared to the antidepressant properties of (±)-1-(3,4-dichlorophenyl)-3-azabicyclo[3.1.0]hexane hydrochloride using a standard norepinephrine transporter binding assay.

6.1.1. MATERIALS AND METHODS

The norepinephrine binding assay was performed according to the methods described in Raisman et al., *Eur. J. Pharmacol.* 78:345–351 (1982) and Langer et al., *Eur. J. Pharmacol.* 72:423 (1981). The receptor source was rat forebrain membranes; the radioligand was [$^3$H]-nisoxetine (60–85 Ci/mmol) at a final ligand concentration of 1.0 nM; the non-specific determinant [1.0 μm]; reference compound and positive control were (±)-desmethylimipramine HCl. (+)-1-(3,4-Dichlorophenyl)-3-azabicyclo[3.1.0]hexane HCl was obtained according to the method of Example 5, above. Reactions were carried out in 50 mM TRIS-HCl (pH 7.4), containing 300 mM NaCl and 5 mM KCl at 0° C. to 4° C. for 4 hours. The reaction was terminated by rapid vacuum filtration onto glass fiber filters. Radioactivity trapped in the filters was determined and compared to control values in order to ascertain the interactions of the test compound with the norepinephrine uptake site. The data are reported in Table 1 below.

6.1.2. RESULTS

TABLE 1

| Norepinephrine Transporter Binding Assay | |
|---|---|
| Compound | Ki |
| (±)-1-(3,4-dichlorophenyl)-3-azabicyclo[3.1.0]hexane HCl | $1.42 \times 10^{-7}$ |
| (+)-1-(3,4-dichlorophenyl)-3-azabicyclo[3.1.0]hexane HCl | $8.20 \times 10^{-8}$ |
| (±)-desmethylimiprimine HCl | $1.13 \times 10^{-9}$ |

The data in Table 1 show that (+)-1-(3,4-dichlorophenyl)-3-azabicyclo[3.1.0]hexane HCl has a significantly greater affinity for the norepinephrine uptake site than does the (±)-1-(3,4-dichlorophenyl)-3-azabicyclo[3.1.0]hexane HCl.

Successful inhibition of norepinephrine reuptake has been has been associated with the treatment of one or more of the symptoms of depression (R. J. Baldessarini, *Drugs and the Treatment of Psychiatric Disorders: Depression and Mania,* in Goodman & Gilman's *The Pharmacological Basis of Therapeutics* 431–459 (9$^{th}$ ed. 1996)). Therefore, (+)-1-(3, 4-dichlorophenyl)-3-azabicyclo[3.1.0]hexane or a pharmaceutically acceptable salt thereof will be significantly more active than (±)-1-(3,4-dichlorophenyl)-3-azabicyclo[3.1.0] hexane or a pharmaceutically acceptable salt thereof for treating of or preventing relapse of depression in a patient.

6.2. SEROTONIN TRANSPORTER BINDING ASSAY

The anti-depressant properties of (+)-1-(3,4-dichlorophenyl)-3-azabicyclo[3.1.0]hexane hydrochloride were compared to the anti-depressant properties of (±)-1-(3,4-dichlorophenyl)-3-azabicyclo[3.1.0] hexane hydrochloride using a standard serotonin transporter binding assay.

6.2.1. MATERIALS AND METHODS

The serotonin binding assay was performed according to the methods described in D'Amato et al., *J. Pharmacol. Exp. Ther.* 242:364–371 (1987) and Brown et al., *Eur. J. Pharmac.* 123:161–165 (1986). The receptor source was rat forebrain membranes; the radioligand was [$^3$H]-citalopram (70–87 Ci/mmol) with a final ligand concentration of 0.7 nM; the non-specific determinant was clomipramine [10 μm]; and the reference compound and positive control were (±)-desmethylimipramine. (+)-1-(3,4-Dichlorophenyl)-3-azabicyclo[3.1.0]hexane HCl was obtained according to the method of Example 5, above. Reactions were carried out in 50 mM TRIS-HCl (pH 7.4) containing 120 mM NaCl and 5 mM KCl at 25° C. for 60 minutes. The reaction was terminated by rapid vacuum filtration onto glass fiber filters. Radioactivity trapped in the filters was determined using liquid scintillation spectrometry and compared to control values in order to ascertain any interactions of test compound with the serotonin transporter binding site. The data are reported in Table 2 below.

6.2.2 RESULTS

TABLE 2

Serotonin Transporter Binding Assay

| Compound | Ki |
| --- | --- |
| (±)-1-(3,4-dichlorophenyl)-3-azabicyclo[3.1.0]hexane HCl | $1.18 \times 10^{-7}$ |
| (+)-1-(3,4-dichlorophenyl)-3-azabicyclo[3.1.0]hexane HCl | $5.08 \times 10^{-8}$ |
| (±)-desmethylimipramine HCl | $2.64 \times 10^{-8}$ |

The data in Table 2 show that (+)-1-(3,4-dichlorophenyl)-3-azabicyclo[3.1.0]hexane HCl has a significantly greater affinity for the serotonin uptake site than does (±)-1-(3,4-dichlorophenyl)-3-azabicyclo[3.1.0]hexane HCl. Successful inhibition of serotonin reuptake has been has been associated with the treatment of one or more of the symptoms of depression (R. J. Baldessarini, *Drugs and the Treatment of Psychiatric Disorders: Depression and Mania,* in Goodman & Gilman's *The Pharmacological Basis of Therapeutics* 431–459 (9$^{th}$ ed. 1996)). Therefore, (+)-1-(3,4-dichlorophenyl)-3-azabicyclo[3.1.0]hexane or a pharmaceutically acceptable salt thereof will be significantly more active than (±)-1-(3,4-dichlorophenyl)-3-azabicyclo[3.1.0]hexane or a pharmaceutical salt thereof for treating of or preventing relapse of depression in a patient.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. A method for treating an anxiety disorder in a patient, comprising administering to a patient in need of such treatment an effective amount of (+)-1-(3,4-Dichlorophenyl)-3-azabicyclo[3.1.0]hexane or a pharmaceutically acceptable salt thereof, each being substantially free of its corresponding (−)-enantiomer.

2. The method according to claim 1, wherein (+)-1-(3,4-Dichlorophenyl)-3-azabicyclo[3.1.0]hexane or pharmaceutically acceptable salt thereof has no more than about 2% w/w of the corresponding (−)-enantiomer.

3. The method according to claim 1, wherein the (+)-1-(3,4Dichlorophenyl)-3-azabicyclo[3.1.0]hexane or pharmaceutically acceptable salt thereof has no more than about 1% w/w of the corresponding (−)-enantiomer.

4. The method of claim 1, wherein the anxiety disorder is selected from the group consisting of Panic Disorder, Panic Attack, Agoraphobia, Generalized Anxiety Disorder, Obsessive-Compulsive Disorders, Phobic Disorders and Post-Traumatic Stress Disorders.

5. The method of claim 2, wherein the anxiety disorder is selected from the group consisting of Panic Disorder, Panic Attack, Agoraphobia, Generalized Anxiety Disorder, Obsessive-Compulsive Disorders, Phobic Disorders and Post-Traumatic Stress Disorders.

6. The method of claim 3, wherein the anxiety disorder is selected from the group consisting of Panic Disorder, Panic Attack, Agoraphobia, Generalized Anxiety Disorder, Obsessive-Compulsive Disorders, Phobic Disorders and Post-Traumatic Stress Disorders.

7. A method for treating an eating disorder in a patient, comprising administering to a patient in need of such treatment an effective amount of (+)-1-(3,4-Dichlorophenyl)-3-azabicyclo[3.1.0]hexane.

8. The method according to claim 7, wherein the (+)-1-(3,4Dichlorophenyl)-3-azabicyclo[3.1.0]hexane or pharmaceutically acceptable salt thereof has no more than about 2% w/w of the corresponding (−)-enantiomer.

9. The method according to claim 7, wherein the (+)-1-(3,4Dichlorophenyl)-3-azabicyclo[3.1.0]hexane or pharmaceutically acceptable salt thereof has no more than about 1% w/w of the corresponding (−)-enantiomer.

10. The method of claim 7, wherein the eating disorder is selected from the group consisting of Anorexia Nervosa, Binge-Eating Disorder, Bulimia Nervosa—Nonpurging Type and Bulimia Nervosa—Purging Type.

11. The method of claim 8, wherein the eating disorder is selected from the group consisting of Anorexia Nervosa, Binge-Eating Disorder; Bulimia Nervosa—Nonpurging Type and Bulimia Nervosa—Purging Type.

12. The method of claim 9, wherein the eating disorder is selected from the group consisting of Anorexia Nervosa, Binge-Eating Disorder, Bulimia Nervosa—Nonpurging Type and Bulimia Nervosa—Purging Type.

13. A method for treating a urinary incontinence disorder in a patient, comprising administering to a patient in need of such treatment an effective amount of (+)-1-(3,4-Dichlorophenyl)-3-azabicyclo[3.1.0]hexane or a pharmaceutically acceptable salt thereof, each being substantially free of its corresponding (−)-enantiomer.

14. The method according to claim 13, wherein the (+)-1-(3,4Dichlorophenyl)-3-azabicyclo[3.1.0]hexane or pharmaceutically acceptable salt thereof has no more than about 2% w/w of the corresponding (−)-enantiomer.

15. The method according to claim 13, wherein the (+)-1-(3,4-Dichlorophenyl)-3-azabicyclo[3.1.0]hexane or pharmaceutically acceptable salt thereof has no more than about 1% w/w of the corresponding (−)-enantiomer.

16. The method of claim 13, wherein the urinary incontinence disorder is selected from the group consisting of Urge Incontinence; Stress Incontinence, Overflow Incontinence, Functional Incontinence, Neurogenic Incontinence and Post-Prostatectomy Incontinence.

17. The method of claim 14, wherein the urinary incontinence disorder is selected from the group consisting of Urge Incontinence, Stress Incontinence, Overflow Incontinence, Functional Incontinence, Neurogenic Incontinence and Post-Prostatectomy Incontinence.

18. The method of claim 15, wherein the urinary incontinence disorder is selected from the group consisting of Urge Incontinence, Stress Incontinence, Overflow Incontinence, Functional Incontinence, Neurogenic Incontinence and Post-Prostatectomy Incontinence.

* * * * *